(12) United States Patent
Li

(10) Patent No.: US 11,179,281 B2
(45) Date of Patent: Nov. 23, 2021

(54) MULTILAYER-STRUCTURE ABSORBENT CORE FOR NURSING PAD, AND METHOD FOR PREPARING ABSORBENT CORE

(71) Applicant: BEIJING BEISHUTE MATERNITY & CHILD ARTICLES CO., LTD, Beijing (CN)

(72) Inventor: Qiuhong Li, Beijing (CN)

(73) Assignee: Beijing Beishute Maternity & Child Articles Co., Ltd.

( * ) Notice: Subject to any disclaimer, the term of this patent is extended or adjusted under 35 U.S.C. 154(b) by 809 days.

(21) Appl. No.: 14/277,947

(22) Filed: May 15, 2014

(65) Prior Publication Data
US 2015/0209196 A1 Jul. 30, 2015

(30) Foreign Application Priority Data

Jan. 24, 2014 (CN) .......................... 201410036303.9

(51) Int. Cl.
*A61F 13/15* (2006.01)
*A61F 13/53* (2006.01)
(Continued)

(52) U.S. Cl.
CPC ........ *A61F 13/53* (2013.01); *A61F 13/15707* (2013.01); *A61F 13/539* (2013.01);
(Continued)

(58) Field of Classification Search
CPC .. A61F 13/53; A61F 13/15707; A61F 13/539; A61F 13/141; A61F 13/143;
(Continued)

(56) References Cited

U.S. PATENT DOCUMENTS 5,427,838 A 6/1995 Yamamoto et al.
5,613,960 A 3/1997 Mizutani
(Continued)

FOREIGN PATENT DOCUMENTS

CN 2190497 5/1994
CN 101061978 10/2007
(Continued)

*Primary Examiner* — Jacqueline F Stephens
(74) *Attorney, Agent, or Firm* — Barnes & Thornburg LLP

(57) ABSTRACT

The invention provides a multilayer-structure absorbent core for a disposable absorbent article, and a method for preparing the absorbent core, wherein the absorbent core is compacted and formed by each layer; its surface presents a grid-shaped groove; the depth at the intersection point of the grid-shaped groove is bigger than that at the non-intersection point thereof. The invention adopts a new synchronous split-level process; that is, a linear grid-shaped trapezoid-shaped compaction mechanism, of which the height is smaller than that of a circular-platform structure, incompletely compacts the absorbent core and separates the absorbent core into numerous small convex spaces, while a circular-platform structure carries out the dot-shaped compaction for the absorbent core. Under the conditions that the liquid-absorption functions of a deflector layer and a reservoir layer are maintained, the movement of polymer water-absorption material is completely limited while the strength of a core body is enhanced. The invention adjusts the structure of the core body and a process of preparing it, thus facilitating the improved multilayer structure to have more liquid-absorption amount, faster liquid-absorption speed and increased strength.

12 Claims, 6 Drawing Sheets

(51) Int. Cl.
  *B30B 11/16* (2006.01)
  *A61F 13/539* (2006.01)
  *B30B 3/04* (2006.01)

(52) U.S. Cl.
  CPC .............. *B30B 3/04* (2013.01); *B30B 11/165* (2013.01); *A61F 2013/530007* (2013.01); *A61F 2013/530116* (2013.01); *A61F 2013/530124* (2013.01); *Y10T 428/24612* (2015.01)

(58) Field of Classification Search
  CPC ........ A61F 13/145; A61F 2013/530116; A61F 2013/530124; B30B 3/04; B30B 11/165
  See application file for complete search history.

(56) References Cited

U.S. PATENT DOCUMENTS

| | | |
|---|---|---|
| 5,637,106 A | 6/1997 | Mitchell et al. |
| 9,108,355 B2 | 8/2015 | Kume et al. |
| 2007/0093164 A1* | 4/2007 | Nakaoka ............... A61F 13/536 442/385 |
| 2008/0281287 A1 | 11/2008 | Marcelo et al. |

FOREIGN PATENT DOCUMENTS

| | | |
|---|---|---|
| CN | 101273933 | 10/2008 |
| CN | 101301243 | 11/2008 |
| CN | 101970211 | 2/2011 |
| CN | 201959103 U | 9/2011 |
| CN | 102245141 | 11/2011 |
| CN | 202409290 U | 9/2012 |
| CN | 203935331 U | 11/2014 |

* cited by examiner

MULTILAYER-STRUCTURE ABSORBENT CORE FOR NURSING PAD, AND METHOD FOR PREPARING ABSORBENT CORE

CROSS-REFERENCE TO RELATED APPLICATIONS

This disclosure claims the benefit of priority to CN Patent Application No. 201410036303.9, filed 24 Jan. 2014, the disclosure of which is incorporated herein in its entirety.

FIELD OF THE INVENTION

The invention belongs to the field of a health and nursing article, and relates to an absorbent core for a disposable absorbent article (particularly a nursing pad), specifically to the absorbent core with a multilayer complex liquid-absorption structure for the disposable absorbent article (particularly the nursing pad). The invention also relates to a method for preparing the absorbent core, specifically to a method for preparing the absorbent core with a synchronous split-level compaction process.

BACKGROUND

The disposable absorbent articles in the prior art (e.g., nursing pads) have many problems when consumers try to use them. For example, a polymer water-absorption material can easily be exposed to the surface of the nursing pad. A severe case is as follows: a polymer water-absorption material exposed to the surface of the nursing pad may rub the skin of the user and hence cause damage to his body. The polymer water-absorption material can agglomerate and ooze out of the surface of the nursing pad after it absorbs liquid. A severe case is as follows: The agglomerated polymer water-absorption material, after absorbing the liquid and pressed heavily by the user, oozes out of the surface of the nursing pad and adheres to the skin of the user, making the user feel unwell. After the nursing pad absorbs liquid, much liquid is not successfully directed in the nursing pad, thus causing the liquid-absorption speed of the absorbent core to be low and causing the nursing pad to be hot and humid. A severe case is as follows: a bedridden patient, as he may not frequently change his nursing pad, suffers from bedsores. The nursing pad can inadequately absorb liquid. Therefore, the nursing pad is required to be frequently replaced during medical care and medical procedures, thus increasing the work load of the nurses. A severe case is as follows: The frequent replacement of nursing pads will increase the suffering of the patient and the work load of the medical staff. Additionally, the tensile strength of the nursing pad is often insufficient to prevent tearing during medical health care and surgery, is often torn. A severe case is as follows: dirty liquid may contaminate bedding articles and may lead to bacterial infection.

The above circumstances often occur in the healthcare industry, due to the reason that the absorbent core of the nursing pad is not satisfying in liquid-absorption amount, liquid-absorption speed and tensile strength.

Therefore, one serious problem to be solved in the production of the nursing pad is to limit the migration of the polymer water-absorption material in the absorbent core. This is because the nursing pad is laid under the body of an user to absorb liquid when in use. When the user turns over, stands up, lies and kicks, the nursing pad will be moved, draped and folded, thus facilitating the polymer water-absorption material in the absorbent core of the nursing pad to be transferred, accumulated, and moved away from a cotton core. When the polymer water-absorption material in the absorbent core of the nursing pad is transferred, accumulated, and moved away from the cotton core, the nursing pad will lose effectiveness, and no longer have the uniform absorbency, thus causing the liquid discharged by the user not to be fully absorbed by the nursing pad, undermining the comfort level of the nursing pad, and severing the illness of the user when the pad's conditions is worse.

In addition, another problem to be solved in the production of the nursing pad it to increase the tensile strength of the absorbent core of the nursing pad. This is because: after the absorbent core of the nursing pad absorbs the liquid, the polymer water-absorption material will be swollen and gelled, thus increasing the strength and tension born by the absorbent core. Meanwhile, the absorbent core is also born by the pressing force and the gravity of the body of the user. When the force born by the absorption core exceeds the tensile strength of the absorbent core itself, the absorbent core will be torn. A severe case is as follows: The absorbent core will pull off the top layer or the bottom layer of the nursing pad, contaminate and damage the body of the user and bedding articles, increase the workload of the nursing staff and make the pad users feel depressed.

However, the process for preparing the absorbent core in the prior art generally adopts a dotted compaction process. As to its principle, certain pressure is applied on the absorbent core, thus facilitating the plant fiber in the absorbent core to be bonded. However, a dot-shaped bonding method or a grid-shaped bonding method is adopted in most of the industrial production. The absorbent core bonded with the dot-shaped bonding method has good diversion and faster liquid-absorption speed. However, as the longitudinal and the transverse tensile strengths of the absorbent core bonded with the dot-shaped bonding method are low, the pressed absorbent core, after absorbing the liquid, is easy to be torn. However, the longitudinal and transverse tensile strengths of the absorbent core bonded with the grid-shaped bonding method are better than those of the absorbent core bonded with the dot-shaped bonding method. However, as the plant fiber in the absorbent core bonded with the grid-shaped bonding method is gridded and compacted, the absorbent core has low diversion and low liquid-absorption speed.

According to the production process in the prior art, a binder, for example, a hot melt adhesive or other glues, is generally added during the industrial production of the absorbent core to bond the materials of each layer of the absorbent core, thus increasing the strength of the absorbent core. However, it is known that if the glue is added in the absorbent core to bond the core, the liquid-absorption amount and the liquid-absorption speed of the absorbent core will be greatly reduced.

SUMMARY

The invention provides a multilayer-structure absorbent core and a process for manufacturing the multilayer-structure absorbent core for a disposable absorbent article. The absorbent article comprises: a top layer, wherein the top layer comprises a thin-type paper layer; a deflector layer, where in the deflector layer comprises a plant fiber layer; an absorbent layer, where in the absorbent layer comprises a polymer water-absorption material layer; a reservoir layer, wherein the reservoir layer comprises a mixed layer of the plant fiber and the polymer water-absorption material; a bottom layer, wherein the bottom layer comprises a thin-type paper layer and/or a non-woven fabric layer; wherein the absorbent layer is disposed between the deflector layer and the reservoir layer; the bottom layer is disposed at the other side of the reservoir layer; the top layer is disposed at the other side of the deflector layer; the surface of the absorbent core compacted and formed by each layer presents grid-shaped grooves; the depth at an intersection point of a grid-shaped groove is bigger than that at the non-intersection point thereof.

BRIEF DESCRIPTION OF THE FIGURES

For a more complete understanding of the disclosure, reference should be made to the following detailed description and accompanying drawing figures wherein.

Figure 1:
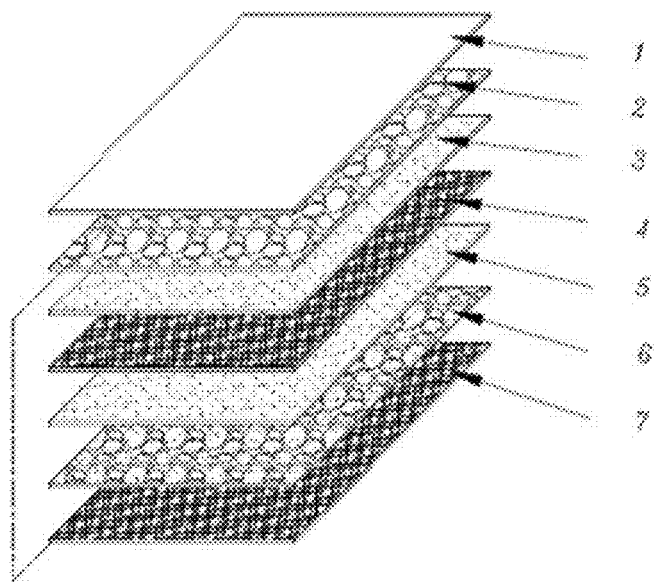
FIG. 1 is a schematic diagram of an embodiment of an absorbent core of the invention, wherein 1: top layer (high strength tissue); 2: deflector layer (pulp fiber); 3: first polymer water-absorption material layer; 4: isolation layer (fluffy non-woven fabric); 5: second polymer water-absorption material layer; 6: reservoir layer (layer mixed with pulp fiber and polymer water-absorption material); 7: bottom layer (high strength tissue or non-woven fabric)

While specific embodiments are illustrated in the figures, with the understanding that the disclosure is intended to be illustrative, these embodiments are not intended to limit the invention described and illustrated herein.

DETAILED DESCRIPTION

In order to reduce or avoid the above inconveniences when a nursing pad is used, the invention carries out targeted improvement for the structure of an absorbent core. With a new synchronized split-level compaction process in the combination of a dot-shaped compaction method and a grid-shaped compaction method, the invention successfully provides a multilayer-structure absorbent core for a disposable absorbent article, and a method for preparing the absorbent core. Even in the case where a binder is not added, the absorbent core of the invention may completely limit a polymer water-absorption material in high percentage not to be transferred in the absorbent core, and facilitate the disposable absorbent article prepared with the absorbent core, particularly the nursing pad, to have the advantages of big liquid-absorption amount, fast liquid-absorption speed, fast liquid diversion, high tensile strength and increased load-bearing performance.

Specifically speaking, the invention provides a multilayer-structure absorbent core for the disposable absorbent article, the absorbent article comprises: a top layer, wherein the top layer comprises a thin-type paper layer; a deflector layer, where in the deflector layer comprises a plant fiber layer; an absorbent layer, where in the absorbent layer comprises a polymer water-absorption material layer; a reservoir layer, wherein the reservoir layer comprises a mixed layer of the plant fiber and the polymer water-absorption material; a bottom layer, wherein the bottom layer comprises a thin-type paper layer and/or a non-woven fabric layer; wherein the absorbent layer is disposed between the deflector layer and the reservoir layer; the bottom layer is disposed at the other side of the reservoir layer; the top layer is disposed at the other side of the deflector layer; the surface of the absorbent core compacted and formed by each layer presents grid-shaped grooves; the depth at an intersection point of a grid-shaped groove is bigger than that at the non-intersection point thereof.

Preferably, the difference between the depth at the intersection point of the groove and that at the non-intersection point thereof is 0.2 mm-1 mm, more preferably 0.4 mm-0.7 mm.

Preferably, the groove at the intersection point is in the reversed circular-platform shape. More preferably, the diameter of a circle of the lower bottom surface of the circular platform is 1 mm-2 mm, preferably 1.2 mm-1.5 mm; further preferably, the included angle of two sides of a thru axis cross section of the circular platform is 25°-60°, preferably 35°-45°.

Preferably, the cross section at the non-intersection point of the grid-shaped groove is in the reversed trapezoid shape. More preferably, the width of the lower bottom edge of the trapezoid is 0.2 mm-2 mm, preferably 0.5 mm-1 mm.

Further preferably, the included angle of two sides of the trapezoid is 25°-60°, preferably 35°-45°.

Preferably, the grid-shaped groove is a square shape groove or a rhombus grid-shaped groove. More preferably, the distance between the centers of the intersection points of two of the adjacent grid-shaped grooves is 2.5 mm-4.5 mm, preferably 3.2 mm-4 mm.

Preferably, the total gram weight of the absorbent core is 50 $g/m^2$-300 $g/m^2$.

Preferably, the thin-type paper layer contained by the top layer is a high strength tissue. Preferably, the gram weight of the thin-type paper layer contained by the top layer is 13 $g/m^2$-20 $g/m^2$.

Preferably, the plant fiber layer contained in the deflector layer also comprises plant fiber removing odor. Preferably, the plant fiber layer contained in the deflector layer also comprises a chemical fiber. Preferably, the gram weight of the plant fiber layer contained by the deflector layer is 10 $g/m^2$-80 $g/m^2$.

Preferably, the polymer water-absorption material contained in the absorbent layer is polyacrylic acid resin. Preferably, the gram weight of the polymer water-absorption material contained in the absorbent layer is 10 $g/m^2$-150 $g/m^2$.

Preferably, the absorbent layer contains a plurality of polymer water-absorption material layers, among which an isolation layer is disposed. More preferably, the isolation layer consists of non-woven fabric. Further preferably, the isolation layer consists of a fluffy non-woven fabric. Preferably, the gram weight of each the polymer water-absorption material layer is 10 $g/m^2$-50 $g/m^2$. Preferably, the gram weight of the non-woven fabric is 10 $g/m^2$-50 $g/m^2$. Preferably, a heatseal adhesive is applied on two sides of the isolation layer. More preferably, the gram weight of the heatseal adhesive is 3 $g/m^2$-4 $g/m^2$.

Preferably, the gram weight of the plant fiber layer contained by the reservoir layer is 10 $g/m^2$-80 $g/m^2$. Preferably, the polymer water-absorption material contained in the reservoir layer is polyacrylic acid resin. Preferably, the gram weight of the polymer water-absorption material layer contained in the reservoir layer is 10 $g/m^2$-50 $g/m^2$. Preferably, the liquid-absorption speed of the polymer water-absorption material contained in the reservoir layer is higher than that contained in the absorbent layer.

Preferably, the thin-type paper layer contained in the bottom layer is a high strength tissue layer. Preferably, the bottom layer contains a thin-type paper layer and a non-woven fabric layer. The thin-type paper layer is disposed between the reservoir layer and the non-woven fabric layer. Preferably, the gram weight of the thin-type paper and/or the non-woven layer is 13 $g/m^2$-20 $g/m^2$.

In the preferred embodiment of the above multilayer-structure absorbent core, the absorbent core comprises: a top layer, wherein the top layer comprises a thin-type paper layer; a deflector layer, wherein the deflector layer comprises a plant fiber layer; an absorbent layer, wherein the absorbent layer comprises a polymer water-absorption material layer; a reservoir layer, wherein the reservoir layer comprises a mixed layer of the plant fiber and the polymer water-absorption material; a bottom layer, wherein the bottom layer comprises a thin-type paper layer and/or a non-woven fabric layer; wherein the absorbent layer is disposed between the deflector layer and the reservoir layer; the bottom layer is disposed at the other side of the reservoir layer; the top layer is disposed at the other side of the deflector layer; the surface of the absorbent core compacted and formed by each layer presents grid-shaped grooves; the depth at an intersection point of a grid-shaped groove is bigger than that at the non-intersection point thereof.

In the preferred embodiment of the above multilayer-structure absorbent core, the absorbent core comprises: a top layer, wherein the top layer comprises a thin-type paper layer; a deflector layer, wherein the deflector layer comprises a plant fiber layer; an absorbent layer, wherein the absorbent layer comprises two or more than two polymer water-absorption material layers and the isolation layer; the isolation layer consists of non-woven fabric, for example the fluffy non-woven fabric, and is disposed between two adjacent polymer water-absorption material layers; a reservoir layer, wherein the reservoir layer comprises a mixed layer of the plant fiber and the polymer water-absorption material; a bottom layer, wherein the bottom layer comprises a thin-type paper layer and/or a non-woven fabric layer; wherein the absorbent layer is disposed between the deflector layer and the reservoir layer; the bottom layer is disposed at the other side of the reservoir layer; the top layer is disposed at the other side of the deflector layer; the surface of the absorbent core compacted and formed by each layer presents grid-shaped grooves; and the depth at an intersection point of a grid-shaped groove is bigger than that at the non-intersection point thereof.

The invention also provides a method for preparing the above multilayer-structure absorbent core. The method comprises compacting each the layer via a pair of compression rollers and forming the absorbent layer, wherein the pair of compression rollers consist of an upper compression roller and a lower compression roller; the surface of the roller body of the upper compression roller has grid-shaped convex; and the height at the intersection point of the grid-shaped convex is bigger than that at the non-intersection point thereof.

Preferably, the difference between the height at the intersection point and that at the non-intersection point is 0.2 mm-1 mm, more preferably 0.4 mm-0.7 mm.

Preferably, the grid-shaped convex is in the circular-platform shape at the intersection point. More preferably, the diameter of the circle of the upper surface of the circular platform is 1 mm-2 mm, preferably 1.2 mm-1.5 mm. Further preferably, the included angle of two sides of a thru axis cross section of the circular platform is 25°-60°, preferably 35°-45°.

Preferably, the cross section of the grid-shaped convex is in the trapezoid shape at the non-intersection point. More preferably, the width of the upper edge of the trapezoid is 0.2 mm-2 mm, preferably 0.5 mm-1 mm. Further preferably, the included angle of two sides of the trapezoid is 25°-60°, preferably 35°-45°.

Preferably, the grid-shaped convex is a square-shape grid-shaped convex or a rhombus grid-shaped convex. More preferably, the distance between the centers of the intersection points of two adjacent grid-shaped convex is 2.5 mm-4.5 mm, preferably 3.2 mm-4 mm.

Preferably, the lower compression roller is a smooth roller with a smooth surface, and its bending deflection is 0.02 mm-0.2 mm, preferably 0.05 mm-0.1 mm.

Preferably, the roller body of the pair of compression rollers is heated by thermal driving oil at the temperature of 120-160° C.

The invention also provides a disposable absorbent article, comprising the above absorbent core or the absorbent core prepared with the above method. Preferably, the disposable absorbent article is a diaper, a home nursing pad, a medical nursing pad, a surgical pad, a weight-bearing nursing pad or an adult incontinence pad.

The invention also provides a nursing pad, comprising the above absorbent core or the absorbent core prepared with the above method. Preferably, the nursing pad is a surgical pad, a medical nursing pad, a weight-bearing nursing pad or an adult incontinence pad.

In a preferred embodiment, the multilayer-structure absorbent layer of the invention is a core body with remarkable properties which is formed through the superposition and compaction of multiple layers of materials. The method for preparing the absorbent core adopts a synchronous split-level compaction process to realize the disposable integral compaction of multiple layers of the materials in the absorbent core while pressing a dot-shaped groove or a grid-shaped groove with a depth being smaller than dot-shaped graph on the absorbent core. Each layer in the absorbent core, with the synchronous split-level compaction process, carries out dot-shaped compaction for the plant fiber in the deflector layer and the reservoir layer in the absorbent core, while a grid-shaped compaction mechanism, with a subcritical molecular bonding principle, incompletely compacts the absorbent core and facilitates the plant fiber in the deflector layer and the reservoir layer to be bonded, thus achieving the objective of the synchronous split-level compaction. The preparation method not only is applied to the absorbent core of the invention but also may be applied to the compaction of the core body of all of absorbent core classes.

As to the plant fiber in the deflector layer in the absorbent core, the fiber is required to be soft, highly fluffy, thick and long and has high adhesive force to the polymer water-absorption material. For example, the plant fiber may be a Kraft sulfate pulp bleached with an ECF method, comprising a fully treated pulp, a semi-treated pulp and an untreated pulp. The amount of plant fiber may be 10 $g/m^2$-80 $g/m^2$.

The deflector layer has one function for directing liquid while may prevent the polymer water-absorption material from leaking out after forming a gel. The deflector layer adopts the plant fiber which has good liquid absorption speed and where the liquid is diffused rapidly. It has the water-absorption ratio being 9-10 times over its own weight, may form a fluffy space in the inner part of the absorbent core, has effective directing and diversion actions, facilitates the absorbed liquid to rapidly penetrate downwards, as well as keeps itself soft and flexible.

The deflector layer adopting the plant fiber has another action preventing polymer water-absorption particles from leaking out to the surface of the top layer after absorbing liquid. The plant fiber may play a role of blocking and separating as well as maintain and improve the softness, dryness and comfortability of the disposable absorbent article.

The deflector layer has another function that the plant fiber in the deflector layer and the reservoir layer is the important implementation body of bonding. A dot-shaped compaction mechanism facilitates each layer of the materials of the absorbent core to form an integral body after being connected while a split-level compaction mechanism separates the absorbent core into many square (or rhombus) areas, both of which are completed based on the bonding of the plant fiber.

The deflector layer has another function of removing odor. When the urine is stored in a nursing pad, it will produce a certain amount of ammonia due to the decomposition of bacteria. However, the ammonia not only has an irritating odor but also has corrosion and irritation effects on the contacted skin. It absorbs the moisture in the skin and results in pressure sores. When the deflector layer uses the pulp with the function of removing the odor, (that is, the pulp has the chemically removing ammonia or physically removing ammonia function after being treated), the ammonia produced in the bacterial decomposition will be absorbed by the pulp removing the odor, which hence reduces the ammonia contents and may reduce the possibility of the occurrence of the bed sores of the user to some extent.

The polymer water-absorption material in the absorbent layer in the absorbent core adopts the resin which may slower the absorption of the moisture, as well as be swollen and gelled. Its main function is to absorb and store liquid directed from the deflector layer. The polymer water-absorption material has high water absorption and water retention, that is, it forms the gel with the water retention after it absorbs water. The weight of the material after absorbing water may be dozens of times more than the self-weight of the material. It is usually produced through moderate cross linkage of the water-soluble polymer. The polymer water-absorption material of the invention may use polyacrylic acid resin-based material and also other highly absorbent materials which are known by a skilled person in the prior art, for example, 7059, 7061 or 7062 made by German company BASF SE. The use mount of the polymer water-absorption material may be 10 $g/m^2$-150 $g/m^2$.

In one preferred embodiment of the absorbent core of the invention, the absorbent layer consists of a first and a second polymer water-absorption material layer, which are separated with one layer of non-woven fabric. After the liquid directed by the plant fiber penetrates to the first polymer absorbent layer, one part of the liquid is absorbed by the polymer water-absorption material of the layer, and the other part of the liquid penetrates to and is absorbed by the second polymer absorbent layer through the gap of the first polymer water-absorption material layer and the non-woven fabric of the isolation layer. The liquid, which may not be absorbed by the polymer water-absorption material layer, is all absorbed by the reservoir layer again. The use amount of the polymer water-absorption material contained in the first polymer absorbent layer is 10 $g/m^2$-50 $g/m^2$. The use amount of the polymer water-absorption material contained in the second polymer absorbent layer is 10 $g/m^2$-50 $g/m^2$.

The isolation layer in the above absorbent core is composed of the non-woven fabric. Preferably, it has characteristics of a highly fluffy fiber structure, fast liquid capture and diffusion capacity, high tensile strength and so on. The isolation layer of the non-woven fabric plays main roles in separating the polymer water-absorption material and reserving the expansion space for the polymer water-absorption material of the absorbent layer, while may prevent the polymer water-absorption material from being gelled and agglomerated after absorbing the liquid. Furthermore, it may enhance the tensile strength of the absorbent core. Preferably, the non-woven fabric is a fluffy non-woven fabric, for example, ES fiber, PP fiber or PET fiber or the combination of one or more; or air-through non-woven fabric, needle-punched non-woven fabric or hot-rolled non-woven fabric or the combination of one or more. Preferably, under the test conditions of pressure of 0.1 kPa-0.5 kPa, the non-woven fabric has the compression rate of over 20%. The basic gram weight of the fluffy non-woven fabric of the invention is within the range of 10 $g/m^2$-50 $g/m^2$.

An usable process is as follows: a small amount of the heatseal adhesive is applied to two sides of the non-woven fabric of the isolation layer, so as to better adhere the polymer water-absorption material of the absorbent layer. However, as the liquid absorption amount of the absorbent core would be affected after the adhesive is applied; the invention does not recommend applying adhesive. If the adhesive is applied, the amount of adhesive shall be controlled with the range of 3 g/m²-4 g/m².

Preferably, the reservoir layer in the above absorbent core is composed of a mixture of plant fiber and the polymer water-absorption material. Its main function is to absorb and store liquid. After the polymer water-absorption material and the plant fiber are mixed, they constitute the reservoir layer and firmly lock the moisture.

As to the plant fiber in the reservoir layer, the fiber is required to be soft, highly fluffy, thick and long and has high adhesive force to the polymer water-absorption material. The plant fiber may be the Kraft sulfate pulp bleached with the ECF method, comprising the fully treated pulp, the semi-treated pulp and the untreated pulp. The amount of the plant fiber may be 10 g/m²-80 g/m².

The polymer water-absorption material in the absorbent layer adopts the resin which may accelerate the absorption of the moisture, as well as be swollen and gelled. The polymer water-absorption material has high water absorption and water retention. The weight of the material after absorbing water may be dozens of times more than the self-weight of the material. It is usually produced through the moderate cross linkage of the water-soluble polymer. It may use polyacrylic acid resin-based material and also other highly absorbent materials which are known by the skilled person in the prior art. The use mount of the polymer water-absorption material may be 10 g/m²-50 g/m².

Compared with the material of the absorbent layer, the absorbent resin in the reservoir layer shall have higher liquid-absorption speed, for example, 60 S and 60 N produced by Japan's Sumitomo Corporation. When the liquid penetrates through the top layer and downwards via the deflector layer, part of the liquid is absorbed by a retarding water-absorption resin in the absorbent layer. The other part of the liquid, which is not being absorbed, continuously penetrates through the reservoir layer and is finally absorbed by the high-speed water-absorption resin in the reservoir layer, thus achieving the result of layered absorption.

In the above absorbent core, the top layer consists of a thin-type paper. The bottom layer may consist of a thin-type paper or a non-woven fabric. Preferably, the thin-type paper is a high strength tissue. The tissue has the function of fast liquid-absorption speed and the properties which improve the tensile strength and anti-friction strength of the absorbent core under wet state, which may reduce the fracture in the surface of a product during use process. Preferably, the top layer of the invention consists of a high strength tissue with the gram weight of 13-20 g/m². The bottom layer of the invention consists of a high strength tissue or the non-woven fabric with the gram weight of 13-20 g/m². The top layer and the bottom layer, after wrapped with two layers of the tissue and the non-woven fabric and via the dotted compaction process, wrap the deflector layer, the absorbent layer, the isolation layer and the reservoir layer, thus facilitating the absorbent core to form one integral body, ensuring the softness, dryness and comfortability of the absorbent core, and improving the strength of the absorbent layer.

Each layer of the absorbent core of the invention adopts a synchronous split-level compaction process; that is, the grid-shaped compaction device incompletely compacts the absorbent core while the absorbent core is carried out with the dot-shaped compaction. A linear grid-shaped trapezoidal body compaction device, of which the height is smaller than the height of a circular-platform body device, incompletely compacts the absorbent core, while the circular-platform body device carries out the dot-shaped compaction for the absorbent core. Meanwhile, the absorbent core of the nursing pad is divided into many small convex spaces, which may limit the transfer of the polymer water-absorption material in the absorbent core of the nursing pad while may improve the strength of the core body. The preparation method is not limited to be applied to a multilayer absorbent core of the invention but may be applied to the compaction of the core body of all of the absorbent core classes.

As to the split-level compaction, engraving device with different heights are utilized to carry out the synchronous compaction for the absorbent core. That is, compared with the dot-shaped compaction device, there is one linear grid-shaped compaction device of which the height is smaller than the height of the dot-shaped compaction device, while the plant fiber in the deflector layer and the reservoir layer in the absorbent core is carried out with the dot-shaped compaction. After the split-level compaction device compacts the absorbent core, the grid-shaped groove may be formed on the surface of the absorbent core; and liquid may rapidly move along the direction of the grid-shaped groove and be rapidly dispersed on the surface of the absorbent core, thus also increasing the liquid-absorption speed by the absorbent core. Part of the plant fiber in the absorbent core is carried out with grid-shaped bonding. The polymer water-absorption material, based on the uniform distribution, is limited to move in the absorbent core. The liquid flowing in the absorbent core is absorbed by multiple layers of the polymer water-absorption materials layer by layer.

Figure 3:
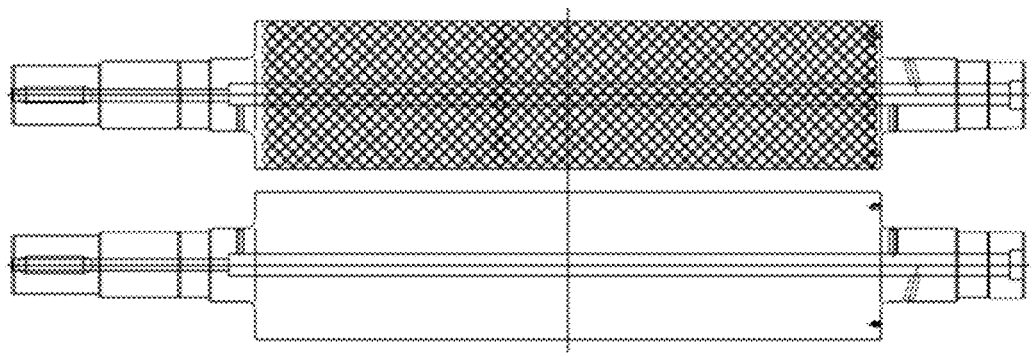
FIG. 3 is a schematic diagram of a pair of compression rollers.
Figure 4:
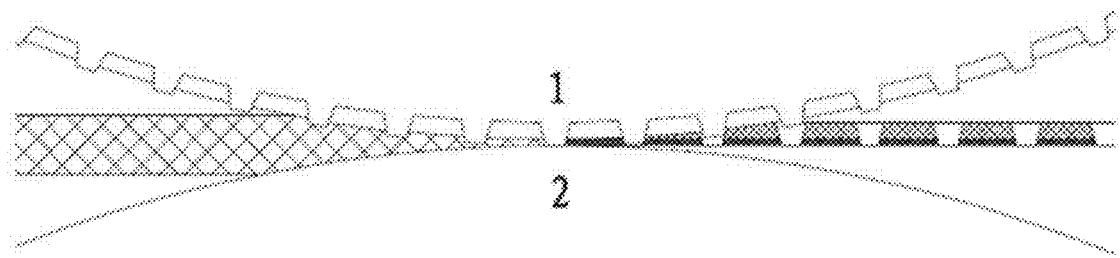
FIG. 4 is a schematic diagram where each layer of an absorbent core is compacted by a pair of compression rollers, wherein 1: upper compression roller; 2: lower compression roller.
Figure 5:
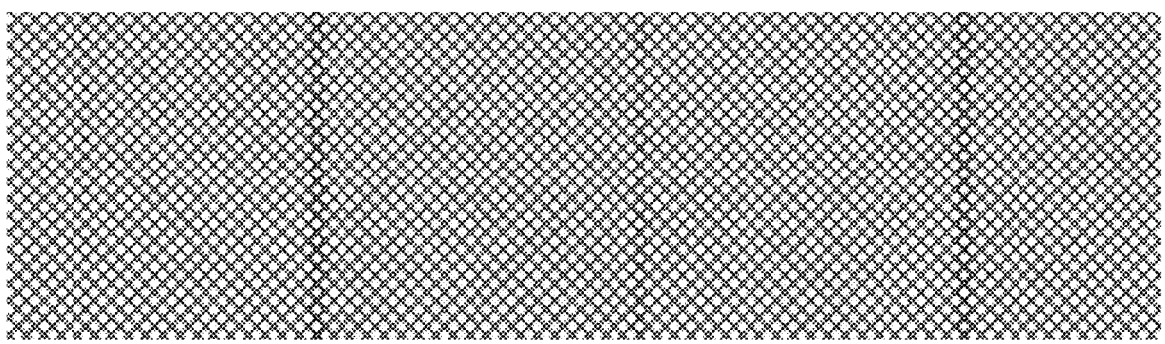
FIG. 5 is an expanded diagram of the surface of an upper compression roller.
Figure 6:
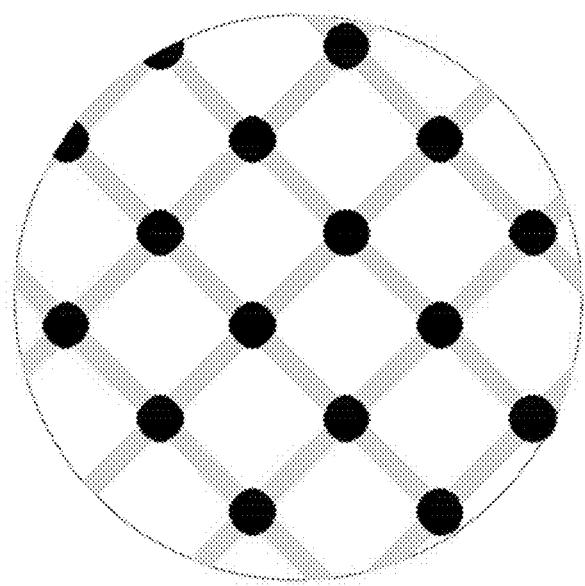
FIG. 6 is a partial enlarged diagram of the surface of an upper compression roller.

Each layer described above adopts a new synchronous split-level compaction process. That is, the absorbent core is incompletely compacted by the linear grid-shaped compaction device while the plant fiber in the deflector layer and the reservoir layer in the absorbent core is bonded by with the dot-shaped compaction, thus facilitating the plant fiber in the deflector layer and in the reservoir layer to be partly bonded, hence keeping the diversion function of the plant fiber in the deflector layer and in the reservoir layer, limiting the movement of the polymer water-absorption material in the absorbent core of the nursing pad, and synchronously increasing the strength of the core body. The process comprises the following detailed steps:

A pair of compression rollers of a compaction device consists of an upper compression roller (a compression dot roller) and a lower compression roller (a smooth roller) which are in up-and-down arrangement (See FIG. 3). The absorbent core is compacted when it passes through the gap between the upper compression roller and the lower compression roller (See FIG. 4). Numerous circular-platform-type convex structures are arranged and combined and forms the upper compression roller (the compression dot roller), which may be in square arrangement (See FIG. 5), rhombus arrangement or other arrangements. The circular-platform-type convex is the main body implementing the compaction of the absorbent core of the nursing pad. When the absorbent core passes through the pair of compression rollers, it produces the pressure of 80-100 Mpa when it is pressed under the weight of the circular-platform-type convex. Meanwhile, the roller body of the pair of compression rollers is heated by thermal oil and under the temperature of 120-160° C. The heated roller body, when the absorbent core passes through the pair of compression rollers and being under the combined action of the pressure and weight, facilitates the plant fiber in the absorbent core to be bonded and form dot-shaped compaction points. Numerous uniformly arranged dot-shaped compaction points are the main body compacted by the absorbent core of the nursing pad (See FIG. 6).

Figure 2:
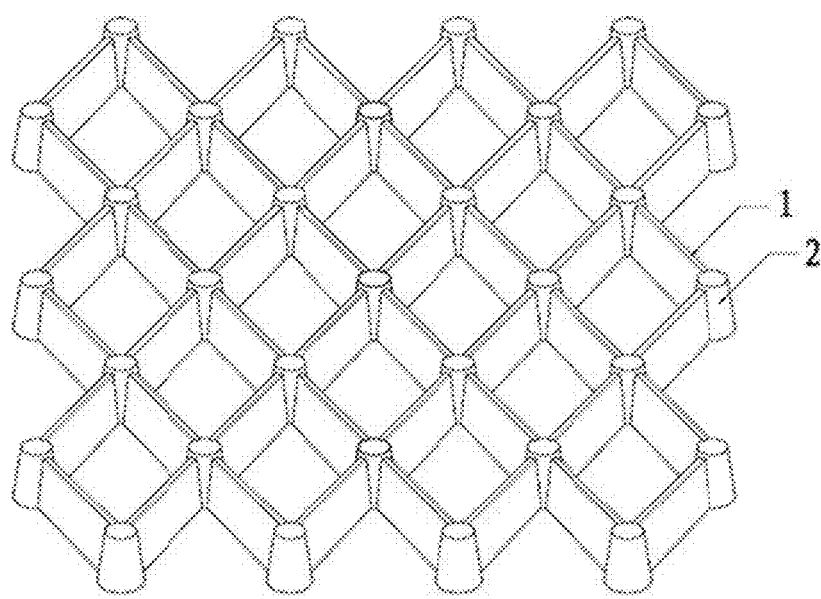
FIG. 2 is an enlarged perspective diagram of a compaction mechanism, wherein 1: trapezoid prismatic body; 2: circular platform.

A trapezoid device, connecting the circular-platform-type convex device on the surface of the roller body, is another key component of the invention implementing the compaction (See FIG. 2). The trapezoid device takes the circular-platform-shaped convex device as the center, and extends and connects four adjacent circular-platform-shaped convex devices, thus forming each and every one of adjacent small square (or rhombus) areas. The compaction device is characterized in that on the expanded surface of the roller body, the height of the circular-platform-type convex device is bigger than that of the trapezoid device. The plant fiber in the absorbent core of the nursing pad, after being pressed by the trapezoid device and also because the height of the circular-platform-type convex device is bigger than that of the trapezoid device, is not fully compacted by a trapezoid structure of the surface of the roller body and hence result in an incomplete compaction state. The compaction part of numerous adjacent trapezoid devices under incomplete compaction state separates the absorbent core into numerous small square (or rhombus) areas. The polymer water-absorption material mixed in the plant fiber of the absorbent core is hence limited in the small square (or rhombus) area, thus achieving the objective of limiting the transfer of the polymer water-absorption material during the process that the user uses the nursing pad.

The circular-platform-type convex device is a circular platform of which two sides of the thru axis cross section form the angle of 25°-60°, preferably 35°-45°. The reason why the circular-platform-type convex device selects such angle is as follows: when the pair of compression roller is operated, the circular-platform-type convex device may always maintain bigger pressure on the absorbent core. The pressure shall be within the range of 80-100 Mpa. Meanwhile, when the pair of compression rollers run at a high speed, the absorbent core of the nursing pad may rapidly move away from the pair of compression rollers after the compaction, and may not be drawn into the pair of compression rollers by the circular-platform-type convex device again.

The diameter of the circle of the top of the circular-platform-type convex device is within the range of 1 mm-2 mm, preferably 1.2 mm-1.5 mm. The reason why the circular-platform-type convex device selects such range is as follows: if the diameter is too small, the bonding area will be too small, which may not better compact the plant fiber in the absorbent core; however, if the diameter is too big, the bonding area will be too big, thus increasing the compaction area of the absorbent core, causing the hardness of the absorbent core to be too high, influencing the liquid-absorption capacity of the absorbent core, and decreasing the comfortability of the user when in use.

Preferably, the circular-platform-type convex device is in the square (or rhombus) arrangement. The distance between the centers of the adjacent circular-platform-type convex devices is within the range of 2.5 mm-4.5 mm, preferably 3.2 mm-4 mm. The reason why the circular-platform-type convex device selects such range is as follows: the length of the smashed plant fiber is basically within the range of 2.5 mm-2.7 mm. Such distance facilitates the pressed points formed on the absorbent core of the nursing pad by the circular-platform-type convex device to basically fix the two ends of the plant fiber.

The trapezoid device is a prism body of which two sides of the trapezoid cross section forms the angle of 25°-60°, preferably 35°-45°. The reason why the trapezoid device selects such angle is as follows: when the pair of compression rollers is operated, after the circular-platform-type convex device presses on the pressed points on the absorbent core, the trapezoid device may compact most of the uncompacted plant fiber in the absorbent core of the nursing pad of the circular-platform-type convex device, thus separating the absorbent core of the nursing pad into numerous small square (or rhombus) areas.

The width of the top of the trapezoid device is within the range of 0.2 mm-2 mm, preferably 0.5 mm-1 mm. The reason why the trapezoid device selects such range is as follows: too small size may not better compact the plant fiber in the absorbent core while too big diameter may increase the compaction area of the absorbent core, thus causing the hardness of the absorbent core to be too high, affecting the liquid-absorption capacity of the absorbent core, and decreasing the comfortability of the user when in use.

Figure 7:
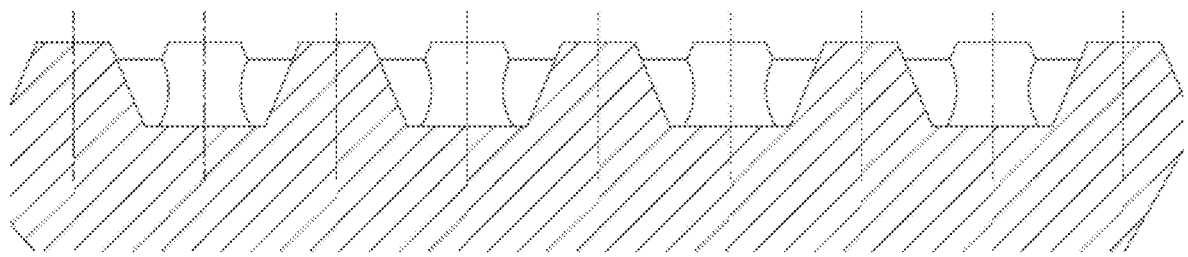
FIG. 7 is a cross section diagram of the surface of an upper compression roller.

The height difference between the heights of the trapezoid device and the circular-platform-type convex device is changed according to the thickness of the nursing pad, and is basically within the range of 0.2 mm-1 mm, preferably 0.4 mm-0.7 mm (See FIG. 7). The unsuitable height difference will cause the plant fiber in the absorbent core fail to be bonded. If the pressed curve line is too deep, the compacted area of the absorbent core will be increased, thus causing the hardness of the absorbent core to be too high, affecting the liquid-absorption capacity of the absorbent core, and decreasing the comfortability of the user when in use. However, if the pressed curve line is too shallow, the trapezoid device may not separate the absorbent core into numerous small square (or rhombus) areas.

The upper compression roller is positioned on the upper part of the pair of compression rollers, wherein its surface is made of alloy steel and has circular-platform-type convex device and the trapezoid device. The circular-platform-type convex is the main body compacting the absorbent core. When the absorbent core passes through the pair of compression rollers and is pressed under the weight of the circular-platform-type convex, it will produce a pressure which is not lower than 80-100 Mpa. Meanwhile, the pair of compression rollers are heated by the thermal oil. In order to ensure that the pair of compression rollers are heated uniformly, the thermal-oil heating method, instead of the conventional heating-rod heating method, is adopted. The heated roller body, when the absorbent core passes through the pair of compression rollers and being under the combined action of the pressure and weight, causes the plant fiber in the absorbent core to be thermally bonded and forms dot-shaped compaction points. Numerous uniformly arranged dot-shaped compaction points are the main body compacted by the absorbent core.

Figure 8:
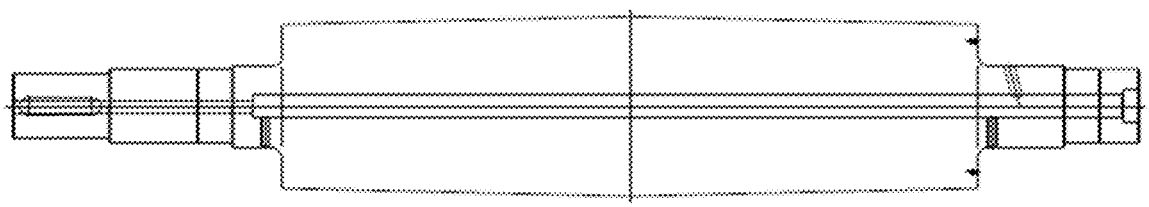
FIG. 8 is a schematic diagram of a lower compression roller.

The compression rollers consist of a lower compression roller and an upper compression roller, which both are used for coordinately completing the compaction of the absorbent core. The lower compression roller is a smooth roller with smooth surface. As the width of the nursing pad is relatively big with a basic size ranging between 600 mm-1200 mm, the lower compression roller shall have certain bending deflection when it is designed (See FIG. 8). The value of the bending deflection is changed with the length of the lower compression roller, and its basic size is within the range of 0.02 mm-0.2 mm, preferably 0.05 mm-0.1 mm.

In the preferred embodiment of the invention, the absorbent core provided in the invention, with a novel structure and in a one-layer structure mixed with the conventional plant fiber and the polymer water-absorption material, is improved as: a multi-layer structure jointly consists of a top layer consisting of tissue, a deflector layer consisting of plant fiber, an absorbent layer consisting of polymer water-absorption material, an isolation layer consisting of non-woven fabric, a reservoir layer mixed with the plant fiber and the polymer water-absorption material, and a bottom layer consisting of the tissue or non-woven fabric. The novel structure at least consists of five layers, and may consist of six layers, seven layers, eight layers or more, wherein the absorbent layer at least consists of one layer of the polymer water-absorption material and also may consist of two layers of the polymer water-absorption material, but the isolation layer needs to be between two layers of the water-absorption material. The similar structures all may be viewed as the extension of the invention. Each layer of the absorbent core of the invention has unique function and may respectively complete packaging, diversion, absorption, isolation, storage and other functions for the liquid. The absorbent core adopts a mechanical dotted bonding compaction device to complete the compaction among multiple layers of the materials. The absorbent core with the novel structure may rapidly direct the liquid and uniformly absorb and store it. The polymer water-absorption material, after it absorbs the liquid, would not be agglomerated or exposed out of the absorbent core, while may improve the tensile strength of the absorbent core at the same time.

In the preferred embodiment of the invention, the invention also provides a method for preparing the absorbent core for the disposable absorbent article, the preparation method comprises the following steps: each layer is disposed in sequence; and the mechanical dotting compaction device is adopted to compact multiple layers. The invention changes the design form of the convex device of the pair of compression rollers, such that the absorbent core passing through the pair of compression rollers, instead of using the original method having only dot-shaped compaction, the current method uses dot-shaped method compressing the plant fibers as well as grid-shaped compaction method partially compressing the plant fibers, so as to facilitate the dot-shaped compaction and the incomplete compaction to jointly take effects on the absorbent core. Eventually, a novel grid-shaped structure is formed on the absorbent core. The absorbent core is separated into numerous small convex spaces. The polymer water-absorption material is completely prevented from moving inside the absorbent core. In addition, visually, the product presents a pattern of numerous small convex squares, rhombuses or other patterns, thus offering a completely new vision to the user. The invention is a method for preparing the nursing pad conforming to the industrial development trend. The absorbent core, after being dotted and solidified with a new process, may prevent the inner polymer material from transferring in the absorbent core. Furthermore, the tissue is prevented from being gelled, bonded, and compacted through with hard points while the proportion of the polymer material in the plant fiber may be increased. The proportion of the polymer material in the absorbent core is increased and results in increasing the whole liquid-absorbent capacity of the absorbent core as well.

The absorbent core of the invention is suitable for a disposable absorbent article, especially various nursing pads, preferably a surgical pad, a medical nursing pad, a weight-bearing nursing pad used by the user with heavier weight, an adult incontinence pad and so on. The absorbent core of the invention may uniformly and dispersedly absorb and store liquid as well as facilitate the absorbent core of the nursing pad to have superior absorption capacity, larger tensile strength as well as keeping the pad a soft, dry and comfortable surface, while improving the tensile strength of the absorbent core of the nursing pad.

The invention increases the liquid-absorption amount of the absorbent core. Compared with the conventional absorbent core, the invention applies polymer water-absorption material in the absorbent core through multiple layers, so as to improve the applied amount of the polymer water-absorption material. Part of the plant fiber in the absorbent core of the invention is processed out with grid-shaped bonding. The polymer water-absorption material, based on the uniform distribution inside the absorbent core, is limited to move in the absorbent core.

The invention increases the liquid diversion function of the absorbent core. The invention, while carries out grid-shaped partial bonding of the plant fiber, may maintain a part of the plant fiber in the absorbent core not to be bonded, so as to maintain the liquid diversion function of the plant fiber. Meanwhile, a middle layer may also select a material with great diversion. Furthermore, a first polymer water-absorption material selects the material with great penetrativity to maintain the great diversion function of the absorbent core.

The invention increases the tensile strength of the absorbent core. The non-woven material is added into the middle place of the polymer water-absorption layer in the absorbent core. The bottom layer of the absorbent core is made of the non-woven material or the high-strength tissue. Meanwhile, the plant fiber adopted in the invention, part of which is carried out with the grid-shaped bonding, may also improve the tensile strength of the absorbent core.

In order to achieve a novel structure for the above purpose, FIG. 1 shows a structure of one embodiment of the invention. The structure of the absorbent core is adjusted to facilitate the absorbent core to have a multilayer complex layered liquid-absorption structure including a tissue top layer, a plant fiber deflector layer, a first polymer water-absorption material layer, a non-woven fabric isolation layer, the second polymer water-absorption material, a reservoir layer having a mixture of plant fiber and polymer water-absorption material, a tissue or non-woven bottom layer and so on.

With the physical characteristics of each layer of the material of the invention, the liquid may be successfully directed during the process as the liquid flows in the absorbent core. The liquid flowing in the absorbent core is absorbed by multiple layers of the polymer water-absorption materials layer by layer. The materials of the non-woven fabric and the high strength tissue in the absorbent core may improve the strength of the core body. The structure of the material of the invention is to solve various problems which often occur during the process when the conventional absorbent core is used: i.e., the polymer water-absorption material is easy to be exposed on the surface of the nursing pad; the polymer; the polymer water-absorption material, after it absorbs the liquid, is gelled, and is pressed by the user, is penetrated out and adheres to the body of the user; the absorbent core has low liquid-absorption speed, small liquid-absorption amount, low tensile strength, and so on.

The absorbent core of the invention has the following technical effects: The tissue top layer and the tissue or non-woven fabric bottom layer wrap the absorbent core and increase the tensile strength of the absorbent core. The plant fiber deflector layer may rapidly direct the liquid and prevent the polymer water-absorption material at its lower layer from penetrating out. The first polymer water-absorption material may slowly absorb the liquid and facilitate the liquid to easily pass through. The deflector absorbent layer of the non-woven fabric has the action of separating the absorbent layer, may have rapid diversion and may improve the strength of the absorbent core. Meanwhile, the nonwoven fabric layer may also reserve enough expansion space for the polymer water-absorption material after it absorbs the liquid. The second polymer water-absorption material may rapidly absorb the liquid and facilitate the liquid to easily pass through. The reservoir layer mixed with the plant fiber and the polymer water-absorption material may rapidly absorb, lock and direct the liquid.

Specifically, this structure has one advantage that it may accelerate the diversion speed of the absorbent core. The plant fiber in the deflector layer of the absorbent core of the invention may accelerate the diversion of the liquid while storing the liquid. The non-woven fabric isolation layer between the absorbent layers in the absorbent core selects the non-woven fabric with better diversion and may play a role in rapid diversion of the liquid as well. The plant fiber in the reservoir layer mixed with the plant fiber and the polymer water-absorption material in the absorbent core may also rapidly direct the liquid. Meanwhile, as the polymer water-absorption material in the absorbent layer uses the material through which the liquid is easily passed, it may also successfully direct the liquid.

This structure has another advantage of increased liquid-absorption amount of the absorbent core. The polymer material in the absorbent core of the invention may be disposed into multiple layers. Two adjacent polymer absorbent layers in the absorbent layer may be separated through the non-woven isolation layer. As the used non-woven fabric has fluffiness and may be reserved with the space expanded after the polymer material absorbs the liquid, the polymer material applied of the invention may reach its own maximum liquid-absorption amount. The structure of the absorbent core of the invention may be disposed to have multiple polymer absorbent layers. Compared with the conventional single-layer structure, this structure has high utilization rate for the polymer material. The invention may also increase the applied amount of each layer of the polymer material in the absorbent core, so as to increase the liquid-absorption amount of the absorbent core.

This structure also has one advantage that the multilayer polymer material utilizes the physical properties of its material and adopts the differential absorption principle. That is, each layer of the polymer material has different liquid-absorption speed. The polymer material with slow liquid-absorption speed, for example, 7059, 7061 and 7062 produced by Germany BASF SE Company, is disposed at one side of the plant fiber deflector layer. The polymer material with fast liquid-absorption speed, for example, 60S and 60N produced by Japan's Sumitomo Corporation, is disposed at one side of the bottom layer of the absorbent core. Each layer of the polymer material, while the liquid is directed by the plant fiber, may absorb the liquid according to the respective liquid-absorption speeds, thus achieving the rapid and uniform liquid-absorption function of the absorbent core.

This structure has another advantage of increased tensile strength of the absorbent core. The top layer, the isolation layer or the bottom layer of the invention is made of non-woven fabric or high strength tissue. The non-woven fabric or the high strength tissue may greatly increase the tensile strength of the absorbent core and facilitates the absorbent core to have greatly increased tensile strength in the transverse and the longitudinal directions.

The absorbent core uses many materials and combinations. However, the absorbent core, with any combination, shall be used for a health article only after it is compacted. The objective of the compaction is to have the process facilitating each layer of the materials to form one integral absorbent core.

The liquid-absorption amount, the liquid-absorption speed and other quality properties of the products of the absorbent core have close relation with the compaction of the absorbent core. The absorbent core also has many kinds of the conventional compaction processes too. However, basically, these processes may be classed into a line-shaped compaction and the dot-shaped compaction. If the absorbent core is carried out with the line-shaped compaction, its compaction area is big. However, as the compaction area of the absorbent core is big, the plant fiber in the absorbent core is damaged; the liquid-absorption speed of the absorbent core is lowered; the polymer absorbent material, which absorbs the liquid, does not have enough expansion space; and the liquid-absorption amount of the absorbent core is decreased. If the absorbent core is carried out with dot-shaped compaction, the compaction area is small; the plant fiber in the absorbent core has great diversion; and the liquid-absorption speed of the absorbent core is increased. However, the absorbent core with smaller compaction area, when in used, usually has one problem that the polymer water-absorption material is easily to move and accumulate. The problem known in the industry is as follows: after the polymer water-absorption material is transferred and accumulated, the liquid-absorption amount, the liquid-absorption speed, the comfortability and practicability of the absorbent core are also decreased. The compaction of the absorbent core shall meet the following conditions: the movement of the polymer water-absorption material in the absorbent core is limited, and the compaction area shall be the minimum.

The product of the absorbent core is usually compacted with a compression and bonding method of the plant fiber. Embodiments of the Invention are as follows: The molecules of the plant fiber in the absorbent core, under certain pressure and temperature, are bonded and connected with the molecules of other materials within the pressure area as a whole. They are not separated even when the pressure and the temperature actions are eliminated, thus facilitating each layer of the materials of the absorbent core to be connected as a whole. Generally speaking, the molecule bonding capacity of the substance made up of the same material is strong. The molecule bonding of any material has one critical point, near which there will be a pressure area (subcritical point) lower than the critical point. Part of the material within this area has the molecule bonding. All of material has the molecule bonding if the critical point is exceeded.

With the above principle, the invention adopts the dot-shaped bonding method to compact the absorbent core while adopting the line-shaped bonding method to partially compact the absorbent core. The partial compaction may facilitate the plant fiber to be under the partial bonding state. The plant fiber, which has been carried out with the line-shaped bonding in the transverse and the longitudinal directions, combines the grids and forms locked areas one after another. The polymer water-absorption material may be limited within these areas and may not be moved due to external forces, thus maintaining the excellent absorption function of the polymer material within the absorbent core, and hence keeping the absorbent core to have big liquid-absorption amount. The plant fiber, which is not carried out with the line-shaped bonding, may continuously keep the plant fiber to have sound diversion, while it may not influence the diversion speed of the absorbent core.

Based on the above principle, as to the production process of the absorbent core, the height of the engraved shape of the outer surface of a compaction roller of the absorbent core is needed to be changed. That is, the engraving of the dot-shaped compaction is higher than that of the line-shaped compaction. As the engraving of the line-shaped compaction is lower than that of the dot-shaped compaction (See FIG. 2), the pressure area of which the pressure is lower than the critical point may be produced. As the engraving of the line-shaped compaction is lower than that of the dot-shaped compaction (See FIG. 2), it is called as a synchronous split-level compaction process.

The process for producing the absorbent core combines the synchronous split-level compaction process to achieve the above purpose. As to the split-level compaction, engraving mechanisms with different heights are utilized to carry out the synchronous compaction for the absorbent core. That is, compared with the dot-shaped compaction mechanism, there is one linear grid-shaped compaction mechanism of which the height is smaller than the height of the dot-shaped compaction mechanism, while the plant fiber in the deflector layer and the reservoir layer in the absorbent core is carried out with the dot-shaped compaction. The linear grid-shaped compaction mechanism is called as the split-level compaction mechanism and used for jointly compacting the absorbent core. The linear grid-shaped compaction mechanism utilizes the subcritical molecular bonding principle. However, as the press applied by the linear grid-shaped compaction mechanism is lower than that applied by the dot-shaped compaction mechanism, part of the plant fiber in the deflector layer and the reservoir layer is bonded; that is, the absorbent core may be incompletely compacted. The diversion of the un-bonded plant fiber is maintained while the tensile strength in the transverse and the longitudinal directions of the absorbent core is enhanced.

This split-level compaction mechanism has one advantage of limiting the movement of the polymer water-absorption material. The linear grid-shaped engraving mechanism of the split-level compaction mechanism may separate the absorbent core into numerous connected grid-shaped square (rhombus or other patterns), thus facilitating the polymer water-absorption material to be within each individual square (rhombus or other patterns) area, and hence not to be transferred due to an external force. Compared with the absorbent core under the simple dot-shaped compaction, the polymer water-absorption material in the absorbent core of the invention is not accumulated. Therefore, when the absorbent core starts to absorb the liquid, the polymer water-absorption material uniformly distributed in the square area absorbs the liquid more rapidly. For the same reason, after the polymer water-absorption material is prevented from moving, it also has a better water-locking function after it absorbs the liquid as well as is gelled and pressed.

After the split-level compaction mechanism compacts the absorbent core, the grid-shaped groove may be formed on the surface of the absorbent core. When the absorbent core absorbs the liquid, the liquid may rapidly move along the direction of the grid-shaped groove, thus facilitating the liquid to be rapidly distributed on the surface of the absorbent core and hence increasing the liquid-absorption speed of the absorbent core. The split-level compaction mechanism may compact the grid-shaped groove. Compared with the simple dot-shaped compaction absorbent core, the invention may play a role in rapidly directing the liquid.

The split-level compaction mechanism compacts the absorbent core to be in linear grid shape. The plant fiber in the absorbent core is connected together through the bonding and integrated with the non-woven fabric of the middle layer, thus causing the tensile strength of the absorbent core in the longitudinal and the transverse directions to be increased. Especially after the absorbent core absorbs the liquid, the polymer water-absorption material in the absorbent core is swelled. In a serious case, the polymer water-absorption material, after it absorbs the liquid, tears the absorbent core and is exposed to the outside of the absorbent core. As the absorbent core is carried out with the line-shaped grid-shaped compaction, it has higher integral tensile strength, thus completely avoiding the above conditions to occur.

The split-level compaction mechanism compacts the absorbent core not to facilitate the plant fiber in the absorbent core to be completely compacted, but to facilitate the plant fiber to be under incomplete compaction state. After the absorbent core absorbs the liquid, the un-compacted plant fiber maintains the function of directing the liquid. The advantage of this function is as follows: except the invention, other compaction mechanism of the absorbent core may not possess this function, which is also the primary technical effect of the invention.

This split-level compaction mechanism may limit the polymer water-absorption material not to be moved within the absorbent core. The liquid may rapidly flow in the absorbent core. Meanwhile, the incompletely compacted grid-shaped structure may increase the strength of the core body after it absorbs the liquid. The experiments show that: the multilayer absorbent core with the split-level compaction may rapidly direct the liquid to be uniformly absorbed and stored while may improve the tensile strength of the absorbent core, thus facilitating the disposable absorbent core of the nursing pad to have faster liquid-absorption speed, bigger liquid-absorption amount and higher use strength.

EXAMPLES

Combining the embodiments, the invention is further described in details in the followings. The examples are only used for describing the invention but not for limiting the scope of the invention.

The tables attached to the examples are experimental detection data of an absorbent core for a disposable absorbent article prepared with the examples, wherein the following experiment methods are adopted:

Saturated absorption amount is tested according to the ISO11948 method. Fracture tensile strength is tested according to the ASTM D882 method. The maximum lifting weight is the weight which the absorbent core may bear when the core is lifted, while two or more points of the absorbent core are not torn. The liquid-absorption and the rewetting properties of the absorbent core may be tested with any known method. The testing scope includes all of scopes and sub-scopes.

Example 1

Figure 9:
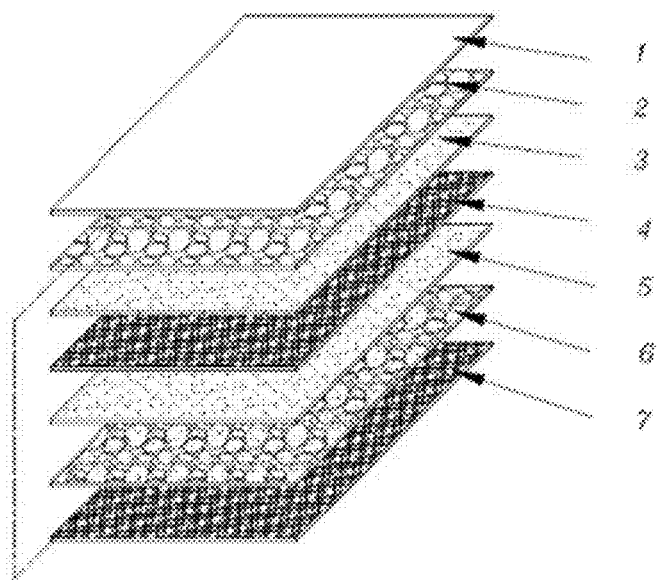
FIG. 9 is a structure diagram of an absorbent core of Example 1, wherein 1: top layer (high strength tissue); 2: deflector layer (pulp fiber); 3: first polymer water-absorption material layer; 4: isolation layer (fluffy non-woven fabric); 5: second polymer water-absorption material layer; 6: reservoir layer (layer mixed with pulp fiber and polymer water-absorption material); 7: bottom layer (high strength tissue)

The structure of an absorbent core of Example 1 is shown in FIG. 9. The gram weight of the absorbent core is 155±10 g/m$^2$, wherein The first layer is a top layer made of a high strength tissue with the gram weight of 20 g/m$^2$; the second layer is a deflector layer made of pulp fiber (for example, semi-treated fluff pulp) with the gram weight of 18 g/m$^2$; the third layer is a first polymer water-absorption material layer made of Super Absorbent Polymers (for example, BASF 7059) with the gram weight of 16 g/m$^2$; the fourth layer is an isolation layer made of a fluffy non-woven fabric with the gram weight of 16 g/m²; the fifth layer is a second polymer water-absorption material layer made of Super Absorbent Polymers (for example, BASF 7059) with the gram weight of 16 g/m²; the sixth layer is a reservoir layer made of a layer mixed with Super Absorbent Polymers (for example, Sumitomo 60S) with the gram weight of 20 g/m² and the pulp fiber (for example, semi-treated fluff pulp) with the gram weight of 35 g/m²; and the seventh layer is a bottom layer made of the high strength tissue with the gram weight of 20 g/m². The test results of the properties of an absorbent core prepared according to Example 1 refer to Table 1.

TABLE 1

Test Results of Properties of Absorbent Core Prepared According to Example 1

| Property Indexes | Experimental Results |
|---|---|
| Maximum Lifting Weight | 350 Pounds |
| Saturated Liquid-Absorption Amount (Saline Solution Test Is 9% Normal Saline) | 3500 ml/m² |
| Liquid-Absorption Rate Value | 250 Seconds |
| Rewetting Value | 3 g |
| Longitudinal Fracture Tensile Strength | 60 ± 20 n/25 mm |
| Transverse Fracture Tensile Strength | 35 ± 15 n/25 mm |

Example 2

Figure 10:
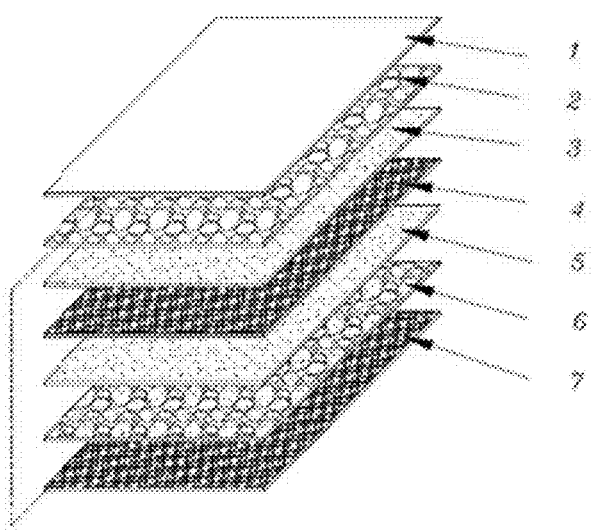
FIG. 10 is a structure diagram of an absorbent core of Example 2, wherein 1: top layer (high strength tissue); 2: deflector layer (pulp fiber); 3: first polymer water-absorption material layer; 4: isolation layer (non-woven fabric); 5: second polymer water-absorption material layer; 6: reservoir layer (layer mixed with pulp fiber and polymer water-absorption material); 7: bottom layer (high strength tissue)

The structure of an absorbent core of Example 2 is shown in FIG. 10. The gram weight of the absorbent core is 155±10 g/m², wherein the first layer is a top layer made of a high strength tissue with the gram weight of 13 g/m²; the second layer is a deflector layer made of pulp fiber (for example, semi-treated fluff pulp) with the gram weight of 20 g/m²; the third layer is a first polymer water-absorption material layer made of Super Absorbent Polymers (for example, BASF 7059) with the gram weight of 18 g/m²; the fourth layer is an isolation layer made of a non-woven fabric with the gram weight of 18 g/m²; the fifth layer is a second polymer water-absorption material layer made of Super Absorbent Polymers (for example, BASF 7059) with the gram weight of 18 g/m²; the sixth layer is a reservoir layer made of a layer mixed with Super Absorbent Polymers (for example, Sumitomo 60S) with the gram weight of 20 g/m² and the pulp fiber (for example, semi-treated fluff pulp) with the gram weight of 35 g/m²; and the seventh layer is a bottom layer made of the high strength tissue with the gram weight of 13 g/m².

Compared with the absorbent core prepared according to Example 1, the absorbent core prepared according to Example 2 replaces the fluffy non-woven fabric of the isolation layer with the non-woven fabric, thus further enhancing the tensile strength of the absorbent core for the disposable absorbent article and improving the bearing property. The test results of the properties of an absorbent core prepared according to Example 2 refer to Table 2.

TABLE 2

Test Results of Properties of Absorbent Core Prepared According to Example 2

| Property Indexes | Experimental Results |
|---|---|
| Maximum Lifting Weight | 450 Pounds |
| Saturated Liquid-Absorption Amount (Saline Solution Test Is 9% Normal Saline) | 3500 ml/m² |
| Rewetting Value | 250 Seconds |

TABLE 2-continued

Test Results of Properties of Absorbent Core Prepared According to Example 2

| Property Indexes | Experimental Results |
|---|---|
| Liquid-Absorption Rate Value | 3 g |
| Longitudinal Fracture Tensile Strength | 70 ± 20 n/25 mm |
| Transverse Fracture Tensile Strength | 45 ± 15 n/25 mm |

Example 3

Figure 11:
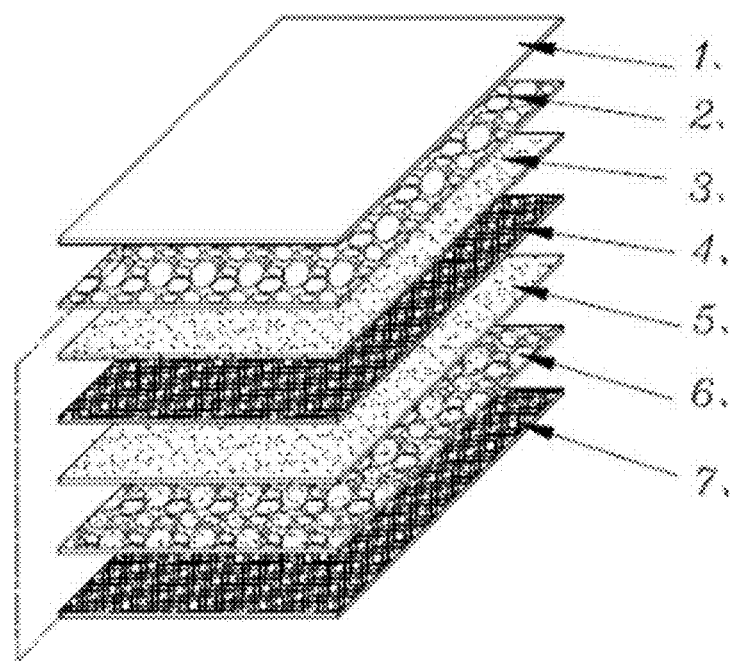
FIG. 11 is a structure diagram of an absorbent core of Example 3, wherein 1: top layer (high strength tissue); 2: deflector layer (pulp fiber); 3: first polymer water-absorption material layer; 4: isolation layer (fluffy non-woven fabric); 5: second polymer water-absorption material layer; 6: reservoir layer (layer mixed with pulp fiber and polymer water-absorption material); 7: bottom layer (non-woven fabric)

The structure of an absorbent core of Example 3 is shown in FIG. 11. The gram weight of the absorbent core is 155±10 g/m², wherein the first layer is a top layer made of a high strength tissue with the gram weight of 13 g/m²; the second layer is a deflector layer made of pulp fiber (for example, semi-treated fluff pulp) with the gram weight of 20 g/m²; the third layer is a first polymer water-absorption material layer made of Super Absorbent Polymers (for example, BASF 7059) with the gram weight of 18 g/m²; the fourth layer is an isolation layer made of a fluffy non-woven fabric with the gram weight of 18 g/m²; the fifth layer is a second polymer water-absorption material layer made of Super Absorbent Polymers (for example, BASF 7059) with the gram weight of 18 g/m²; the sixth layer is a reservoir layer made of a layer mixed with Super Absorbent Polymers (for example, Sumitomo 60S) with the gram weight of 20 g/m² and the pulp fiber (for example, semi-treated fluff pulp) with the gram weight of 35 g/m²; and the seventh layer is a bottom layer made of the non-woven fabric with the gram weight of 13 g/m²;

Compared with the absorbent core prepared according to Example 1, the absorbent core prepared according to Example 3 replaces the bottom layer tissue with the non-woven fabric, thus enhancing the tensile strength of the absorbent core for the disposable absorbent article and improving the bearing property. The test results of the properties of an absorbent core prepared according to Example 3 refer to Table 3.

TABLE 3

Test Results of Properties of Absorbent Core Prepared According to Example 3

| Property Indexes | Experimental Results |
|---|---|
| Maximum Lifting Weight | 400 Pounds |
| Saturated Liquid-Absorption Amount (Saline Solution Test Is 9% Normal Saline) | 3500 ml/m² |
| Rewetting Value | 250 Seconds |
| Liquid-Absorption Rate Value | 3 g |
| Longitudinal Fracture Tensile Strength | 65 ± 20 n/25 mm |
| Transverse Fracture Tensile Strength | 40 ± 15 n/25 mm |

Example 4

Figure 12:
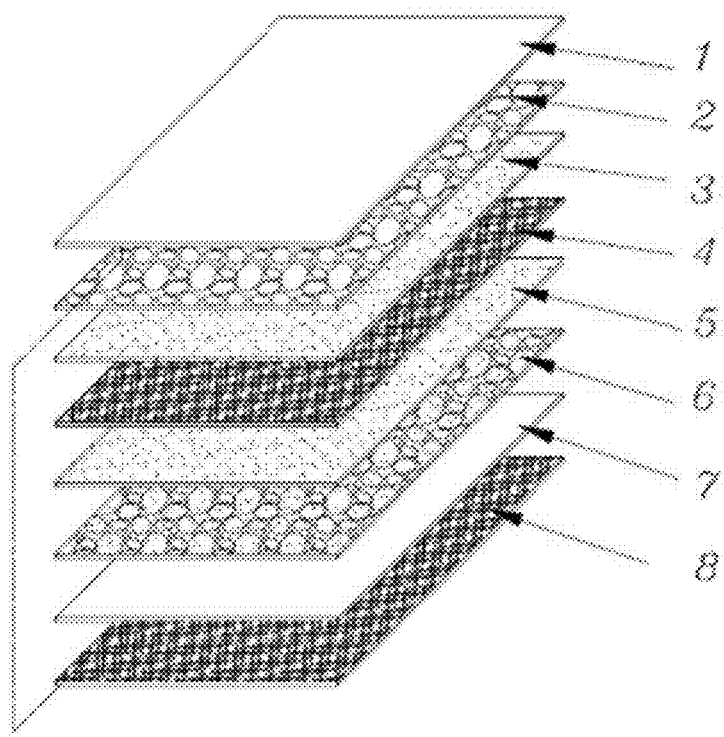
FIG. 12 is a structure diagram of an absorbent core of Example 4, wherein 1: top layer (high strength tissue); 2: deflector layer (pulp fiber); 3: first polymer water-absorption material layer; 4: isolation layer (fluffy non-woven fabric); 5: second polymer water-absorption material layer; 6: reservoir layer (layer mixed with pulp fiber and polymer water-absorption material); 7: bottom layer (high strength tissue), 8: bottom layer (non-woven fabric)

The structure of an absorbent core of Example 4 is shown in FIG. 12. The gram weight of the absorbent core is 170±10 g/m², wherein the first layer is a top layer made of a high strength tissue with the gram weight of 13 g/m²; the second layer is a deflector layer made of pulp fiber (for example, semi-treated fluff pulp) with the gram weight of 20 g/m²; the third layer is a first polymer water-absorption material layer made of Super Absorbent Polymers (for example, BASF 7059) with the gram weight of 18 g/m²; the fourth layer is an isolation layer made of a fluffy non-woven fabric with the gram weight of 18 g/m²; the fifth layer is a second polymer water-absorption material layer made of Super Absorbent Polymers (for example, BASF 7059) with the gram weight of 18 g/m²; the sixth layer is a reservoir layer made of a layer mixed with Super Absorbent Polymers (for example, Sumitomo 60S) with the gram weight of 20 g/m² and the pulp fiber (for example, semi-treated fluff pulp) with the gram weight of 35 g/m²; the seventh layer is a bottom layer made of the high strength tissue with the gram weight of 13 g/m², and the eighth layer is the bottom layer made of the non-woven fabric with the gram weight of 15 g/m².

Compared with the absorbent core prepared according to Example 1, one layer of the non-woven fabric is also found to be added under the bottom layer high-strength tissue, thus greatly enhancing the tensile strength of the absorbent core for the disposable absorbent article and greatly improving the bearing property. The test results of the properties of an absorbent core prepared according to Example 4 refer to Table 4.

TABLE 4

Test Results of Properties of Absorbent Core Prepared According to Example 4

| Property Indexes | Experimental Results |
|---|---|
| Maximum Lifting Weight | 500 Pounds |
| Saturated Liquid-Absorption Amount (Saline Solution Test Is 9% Normal Saline) | 3500 ml/m² |
| Rewetting Value | 250 Seconds |
| Liquid-Absorption Rate Value | 3 g |
| Longitudinal Fracture Tensile Strength | 75 ± 20 n/25 mm |
| Transverse Fracture Tensile Strength | 50 ± 15 n/25 mm |

Example 5

Figure 13:
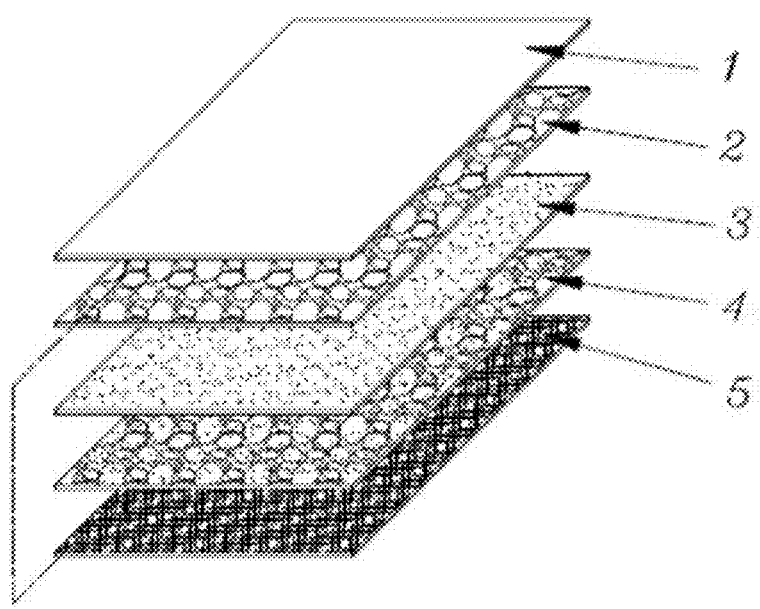
FIG. 13 is a structure diagram of an absorbent core of Example 5, wherein 1: top layer (high strength tissue); 2: deflector layer (pulp fiber); 3: absorbent layer (polymer water-absorption material); 4: reservoir layer (layer mixed with pulp fiber and polymer water-absorption material); 5: bottom layer (non-woven fabric).

The structure of an absorbent core of Example 4 is shown in FIG. 13. The gram weight of the absorbent core is 155±10 g/m², wherein the first layer is a top layer made of a high strength tissue with the gram weight of 18 g/m²; the second layer is a deflector layer made of pulp fiber (for example, semi-treated fluff pulp) with the gram weight of 20 g/m²; the third layer is a polymer water-absorption material layer made of Super Absorbent Polymers (for example, BASF 7059) with the gram weight of 36 g/m²; the fourth layer is a reservoir layer made of a layer mixed with Super Absorbent Polymers (for example, Sumitomo 60S) with the gram weight of 20 g/m² and the pulp fiber (for example, semi-treated fluff pulp) with the gram weight of 45 g/m²; and the fifth layer is a bottom layer made of the non-woven fabric with the gram weight of 18 g/m²;

Compared with the absorbent core prepared according to Example 1, the absorbent core prepared according to Example 5 eliminates the isolation layer, combines two layers of the upper and the lower polymer absorbent layers as one layer of the polymer absorbent layer, and increases the gram weight of the materials of the top layer, the bottom layer and the reservoir layer, which is a simplified process of the invention in the industrialized application. The test results of the properties of an absorbent core prepared according to Example 5 refer to Table 5.

TABLE 5

Test Results of Properties of Absorbent Core Prepared According to Example 5

| Property Indexes | Experimental Results |
|---|---|
| Maximum Lifting Weight | 350 Pounds |
| Saturated Liquid-Absorption Amount (Saline Solution Test Is 9% Normal Saline) | 3500 ml/m² |
| Rewetting Value | 250 Seconds |
| Liquid-Absorption Rate Value | 3 g |
| Longitudinal Fracture Tensile Strength | 55 ± 20 n/25 mm |
| Transverse Fracture Tensile Strength | 30 ± 15 n/25 mm |

What is claimed:

1. A multilayered absorbent core comprising:
a top layer that includes a thin-type paper layer; the top layer carried by
a deflector layer that includes a plant fiber layer; the deflector layer carried by
an absorbent layer that includes a polymer water-absorption material layer; the absorbent layer carried by
a reservoir layer that includes a mixed layer of a plant fiber and a polymer water-absorption material; and the reservoir layer carried by
a bottom layer selected from the group consisting of the thin-type paper layer, a nonwoven fabric layer, or a combination thereof;
the multilayered absorbent core further comprising a top layer surface having a plurality of grooves, wherein one groove intersects another groove at an intersection point, and wherein a first depth of each groove measured between a top of the groove and a bottom of the groove is less than a second depth of the intersection point measured between a top of the intersection point and a bottom of the intersection point.

2. The multilayered absorbent core of claim 1 further comprising a difference between the depth at the intersection point and the depth of the grooves is 0.2 mm to 1 mm.

3. The multilayered absorbent core of claim 1, wherein the intersection point has a reversed circular-platform shape, wherein a diameter of a circle at a bottom surface of the circular platform is 1 mm-2 mm; and wherein an included angle of two sides of a thru axis cross section of the circular platform is 25°-60°.

4. The multilayered absorbent core of claim 1, wherein the plurality of grooves have a shape selected from the group consisting of a reversed trapezoid shape, wherein the trapezoid shape includes a width of a lower bottom edge of the trapezoid of 0.2 mm-2 mm and an included angle of two sides of the trapezoid is 25°-60°;
a square shape; and
a rhombus shape.

5. The multilayered absorbent core of claim 1, wherein a distance between centers of adjacent intersection points 2.5 mm-4.5 mm.

6. The multilayered absorbent core of claim 1, wherein the absorbent core has a weight of 50 g/m²-300 g/m².

7. The multilayered absorbent core of claim 6, wherein the layers are selected from the group consisting of
a thin-type paper layer having a weight of 13 g/m²-20 g/m²;
a plant fiber layer having a weight of 10 g/m²-80 g/m²;
a polymer water-absorption material layer having a weight of 10 g/m²-150 g/m²;
a plant fiber layer having a weight of 10 g/m²-80 g/m²; and
a combination thereof.

8. The multilayered absorbent core of claim 1, wherein the bottom layer includes a thin-type paper layer and a non-woven fabric layer, wherein the thin-type paper layer is disposed between the reservoir layer and the non-woven fabric layer.

9. The multilayered absorbent core of claim 1, wherein the polymer water-absorption material of the reservoir layer is a polyacrylic acid resin.

10. The multilayered absorbent core of claim 1, wherein a liquid-absorption speed of the polymer water-absorption material of the reservoir layer is greater than a liquid-absorption speed of the polymer water-absorption material of the absorbent layer.

11. The multilayered absorbent core of claim 10, wherein the isolation layer comprises a non-woven fabric.

12. The multilayered absorbent core of claim 1 wherein the absorbent layer contains a plurality of polymer water-absorption material layers and an isolation layer disposed between adjacent polymer water-absorption material layers.

\* \* \* \* \*